(12) United States Patent
Andrade et al.

(10) Patent No.: US 11,872,024 B2
(45) Date of Patent: Jan. 16, 2024

(54) METHOD AND SYSTEM FOR NON-INVASIVE MANAGEMENT AND MONITORING OF INTRACRANIAL PRESSURE AND A DEVICE FOR MEASURING OF A SKULL VOLUMETRIC VARIATION

(71) Applicant: Braincare Desenvolvimento e Inovacao Technologica S.A., São Paulo (BR)

(72) Inventors: Rodrigo De Albuquerque Pacheco Andrade, São Carlos (BR); Sergio Mascarenhas Oliveira, São Carlos (BR)

(73) Assignee: BRAINCARE DESENVOLVIMENTO E INOVACAO TECNOLOGICA S.A., São Carlos (BR)

( * ) Notice: Subject to any disclaimer, the term of this patent is extended or adjusted under 35 U.S.C. 154(b) by 200 days.

(21) Appl. No.: 16/178,778

(22) Filed: Nov. 2, 2018

(65) Prior Publication Data

US 2019/0175038 A1 Jun. 13, 2019

(30) Foreign Application Priority Data

Nov. 6, 2017 (BR) .......................... 1020170238792

(51) Int. Cl.
*A61B 5/03* (2006.01)
*A61B 5/00* (2006.01)
(Continued)

(52) U.S. Cl.
CPC ............... *A61B 5/031* (2013.01); *A61B 5/00* (2013.01); *A61B 5/0022* (2013.01); *A61B 5/03* (2013.01);
(Continued)

(58) Field of Classification Search
None
See application file for complete search history.

(56) References Cited

U.S. PATENT DOCUMENTS

| | | | | | |
|---|---|---|---|---|---|
| 3,972,320 | A | * | 8/1976 | Kalman | G08B 25/001 600/519 |
| 2001/0039386 | A1 | * | 11/2001 | Johnson | A61B 5/031 600/561 |

(Continued)

OTHER PUBLICATIONS

International Preliminary Report on Patentability dated Jan. 29, 2019 in corresponding PCT Application No. PCT/IB2018/058635; ISA/BR.

*Primary Examiner* — Alex M Valvis
*Assistant Examiner* — Aurelie H Tu
(74) *Attorney, Agent, or Firm* — Harness, Dickey & Pierce, P.L.C.

(57) ABSTRACT

The present invention describes a method and system for non-invasive management and monitoring of intracranial pressure and a device for measuring of a skull volumetric variation. Specifically, the present invention comprises detecting and receiving the analog signal of the skull volumetric variation of a user, processing its signal and transmitting the processed signal to a pre-configured receiver. The present invention is situated in the technical fields of medicine, biomedicine, neuro science, measuring of physical quantity and electrical engineering.

13 Claims, 21 Drawing Sheets

(51) Int. Cl.
  *A61B 5/369* (2021.01)
  *A61B 5/021* (2006.01)

(52) U.S. Cl.
  CPC ............ *A61B 5/369* (2021.01); *A61B 5/4064* (2013.01); *A61B 5/6803* (2013.01); *A61B 5/6831* (2013.01); *A61B 5/7225* (2013.01); *A61B 5/7246* (2013.01); *A61B 5/021* (2013.01); *A61B 5/6814* (2013.01); *A61B 5/7203* (2013.01); *A61B 5/7221* (2013.01); *A61B 2560/0406* (2013.01)

(56) References Cited

U.S. PATENT DOCUMENTS

| | | | |
|---|---|---|---|
| 2003/0053440 A1* | 3/2003 | Gruhn | H04W 28/06 370/349 |
| 2004/0015058 A1 | 1/2004 | Besson et al. | |
| 2008/0077023 A1 | 3/2008 | Campbell et al. | |
| 2008/0146890 A1* | 6/2008 | LeBoeuf | A61B 5/112 600/300 |
| 2009/0280745 A1* | 11/2009 | Granqvist | A61B 5/0002 455/41.3 |
| 2012/0242501 A1* | 9/2012 | Tran | A61B 5/7465 340/870.02 |
| 2013/0018277 A1* | 1/2013 | Liu | A61B 5/6803 600/561 |
| 2013/0041271 A1* | 2/2013 | Ben-Ari | A61B 5/031 600/506 |
| 2013/0085400 A1* | 4/2013 | Oliveira | A61B 5/11 600/484 |
| 2014/0371545 A1* | 12/2014 | Ben-Ari | A61B 5/6814 600/301 |
| 2016/0000344 A1* | 1/2016 | Cao | A61B 3/16 600/302 |
| 2016/0228064 A1* | 8/2016 | Jung | G06F 1/1684 |
| 2016/0287180 A1* | 10/2016 | Ansari | A61B 5/031 |
| 2017/0164901 A1* | 6/2017 | Shusterman | A61B 5/055 |

* cited by examiner

METHOD AND SYSTEM FOR NON-INVASIVE MANAGEMENT AND MONITORING OF INTRACRANIAL PRESSURE AND A DEVICE FOR MEASURING OF A SKULL VOLUMETRIC VARIATION

CROSS-REFERENCE TO RELATED APPLICATIONS

This application claims the benefit and priority of Brazilian Serial No. 1020170238792 filed Nov. 6, 2017. The entire disclosure of the above application is incorporated herein by reference.

FIELD

The present invention describes a method and system for non-invasive management and monitoring of a skull volumetric variation, and a device for measuring a skull volumetric variation. Specifically it comprises detecting a skull volumetric variation in analog signal, processing this signal and transmitting this signal to another electronic device or to a cloud server. The present invention is situated in the field of medicine, biomedicine, neuroscience, measuring of physical quantity and electrical engineering.

BACKGROUND

The most part of the human organs presents ambient pressure of blood perfusion close to the atmospheric pressure or lower. However, in the central nervous system, that includes the cerebrum and the spinal cord, the ambient pressure is different because it is protected by the cranial cavity and the vertebral canal. This pressure is denominated intracranial pressure.

The intracranial pressure (ICP) is one of the principal physiological parameters in animals and humans and its morphology is extremely important. However, the conventional methods of detecting, monitoring and managing the intracranial pressure of a user is for the most part invasive methods, where the state of art demands non-invasive systems, therefore expanding the research field relating this important neurological parameter, which does not have better research around it because of the invasive method of monitoring the intracranial pressure.

For example, it is well-known of the cardiac variability and other parameters of complexity can predict the clinical state of the patient and the occurrence of fatal events. In patients with neurological risks, the analysis of the correlation between intracranial pressure and arterial pressure offers information about cerebral complacency, which is a crucial fact on the decision-making process on the choice of the best treatment to be applied. However, in practice, rarely the analysis is used to produce relevant information to the hospital staff.

Currently, the monitoring of physiological parameters of patients in intense therapy unities generates a great quantity of data, which usually is underused by the hospital staff, on the decision-making process. The tools currently used, such as alarm protocols of multiparameter monitors, that triggers when physiological parameters deviate from the standard pattern, apparently disrupts more than helps: less than 10% of the emitted alarms in ICUs are clinically relevant. It is estimated that 28% of diagnosis in ICUs in the USA are wrong, 8% of these errors are fatal. In pediatric ICUs, 19.6% of the diagnosis are wrong, 4.5% resulting in fatal errors. Therefore, more than 40 thousand people die annually in ICUs in the USA due to errors on diagnosis.

To optimize treatment protocols, improve the patient quality of life and reduce the errors on diagnosis and hospital expenses, it is necessary to provide better diagnosis tools to the health professionals in order to deliver relevant information about the clinical state of a patient and to assist on the decision-making process. The conventional methods of monitoring intracranial pressure include penetration to the skull and insertion of a catheter to measure ICP. This procedure is invasive and includes risks of aggravating the cerebral edema, hurting the parenchyma, causing a intracerebral hemorrhage and intracranial infection, being the last one the most common to happen. Considering all the mentioned disadvantages, the need to monitor the intracranial pressure with a non-invasive method, that eliminates the generated complications of the skull penetration, is one of great importance, because it opens new research fields around this important physiological parameter, which is not more explored because of the invasive method of monitoring. Furthermore, with the growth of non-invasive monitoring methods, the utility of the invasive method will increase, because of the necessity to confirm the monitoring of absolute intracranial pressure.

A further state of the art need is a system to monitor the intracranial pressure wirelessly, to facilitate the availability of the system in different situations.

A search in scientific and patent literature pointed relevant documents for the present invention, which are described below:

The document WO2013041973A2 shows a system for measuring and monitoring intracranial pressure in a non-invasive way, where the system is connected through cables to monitor the intracranial pressure making the system difficult to be adapted to a plurality of situations and the transport of the equipment could damage the system.

The document CN106618490A shows a minimally invasive system for detecting the temperature and the intracranial pressure of a patient using a different processing method, and sending the signals in a wireless way. The minimally invasive system still needs to be inserted inside the organism of the patient, making it too risky for some situations, or to be used whenever the patient needs. Furthermore, CN106618490A provides a large amount of irrelevant data being transmitted to a receiver, in such a way that the minimally invasive system requires suitable equipment capable to support a high traffic of flow information. This makes the system and process unfeasible to be handled by a user.

The document CN202458347U shows a system for monitoring the intracranial pressure indirectly, where the document shows a method for detecting a plurality of physiological parameters, and the processing of those multiple parameters shows the intracranial pressure of the patient. This system needs the detection of a plurality parameters, and does not detect the intracranial pressure directly, since the applicant emphasizes that the system is adapted to detect blood pressure, electrocardiogram, electroencephalogram, bioimpedance and oxygen of a patient, and then to provide a conclusion about the intracranial pressure of the patient.

The document CN106361320A shows a minimally invasive system for monitoring the intracranial pressure, where the sensor is positioned directly on the skull of a patient, needing a cut on the head of the patient, making this document impracticable to use whenever the patient needs to monitor the intracranial pressure. This solution provides an invasive procedure to collect the information regarding patient health.

As can be inferred from literature, there are no documents suggesting or anticipating the teachings of the present invention, so that the solution proposed here has novelty and inventive step outside the state of the art.

SUMMARY

The present invention solves the technical problems of the state of art by providing a system and method for non-invasive management and monitoring of intracranial pressure and a device for measuring of a skull volumetric variation. Specifically, the present invention comprises detecting and receiving the analog signal of the skull volumetric variation of a user, processing its signal and transmitting the processed signal to a pre-configured receiver by a wireless means. The proposed solution allows a non-invasive detection of skull deformation of a user and the precise monitoring of the intracranial pressure.

In one aspect, the present invention provides a method for non-invasive management and monitoring of intracranial pressure, wherein the method comprises the steps of:
 a. detecting analog signals from a user by a detection device;
 b. receiving the detected analog signals on a receiver, each of the signals being related to the intracranial pressure of the user;
 c. processing by a processor the detected analog signals generating processed signals; and
 d. transmitting the processed signals through a transmitter to a pre-configured receiver, wherein the transmitter and the pre-configured receiver are communicating wirelessly.

In a second aspect, the present invention provides a system for non-invasive management and monitoring of intracranial pressure, wherein the system comprises:
 a. a detection device for detecting analog signals from a skull volumetric variation;
 b. a receiver communicating with the detection device and receiving analog signals related to the intracranial pressure of a user;
 c. a processor comprising at least a tool for processing signals related to the intracranial pressure of the user, wherein the processor is communicating with the receiver; and
 d. a transmitter, wherein the transmitter is communicating with the processor and comprising a module to transmit processed signals wirelessly.

In a third aspect, the present invention provides a device for measuring a skull volumetric variation comprising:
 a. a transducer of variation (8) comprising a detector of variation provided with a first end configured to receive a deflection related to skull volumetric variation, wherein the transducer of variation (8) converts a detected variation on electric signal; and
 b. a housing, wherein the transducer of variation (8) is positioned inside the housing.

These and other aspects of the invention will be immediately appreciated by the well versed in the art, and for companies with interests in the product segment and will be described in sufficient detail to be reproduced in the following description.

DRAWINGS

The examples shown here are intended only to illustrate some of several ways of implement this invention, however, without limiting the scope thereof.

FIGS. 5 to 7 shows an exploded view of an embodiment of the present invention for non-invasive detecting and monitoring of a skull volumetric variation, wherein FIG. 7 shows approximated view of FIG. 5 for better definition of the embodiment.

DETAILED DESCRIPTION

The intracranial pressure is normally lower than 10-15 mmHg in adults, and the intracranial content is protected by the skull, a rigid structure with the internal volume between 1400 to 1700 ml. Under normal conditions, the intracranial content comprises in volume: brain parenchyma from 80% to 85%, cerebrospinal fluid from 5% to 10%, blood from 8% to 12%.

Figure 21:
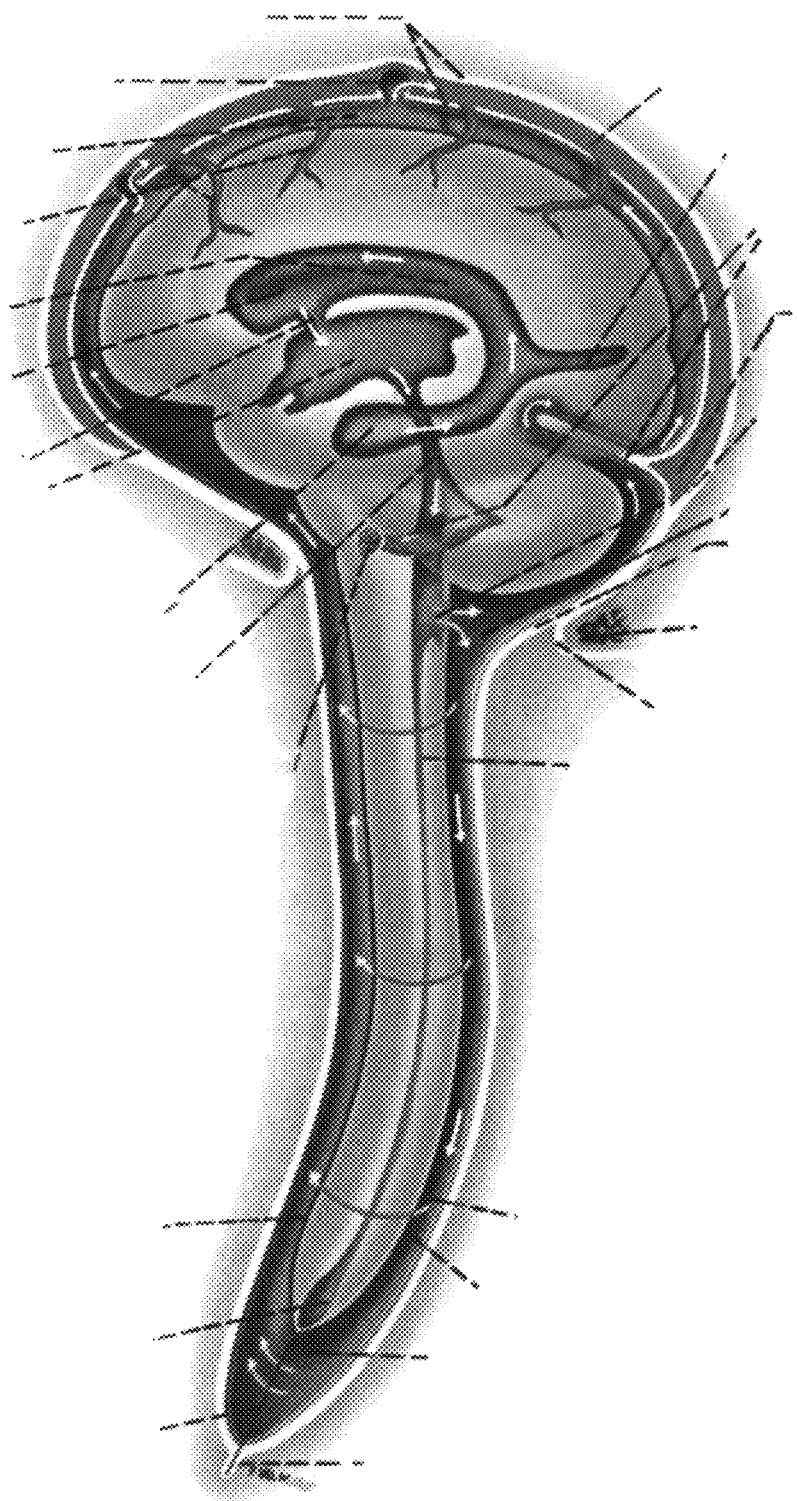
FIG. 21 shows the cerebrospinal fluid circulation in the central nervous system.

The cerebrospinal fluid is a aqueous fluid and colorless, with small quantities of protein, potassium, glucose and sodium chloride that occupies the subarachnoid space and the ventricular cavities, the primal function of the cerebrospinal fluid is to protect the central nervous system, distributing the pressure in virtue of the Pascal principle, equally distributed in all points of skull, as shown on FIG. 21, wherein the arrows shows the direction which the fluid flows through. Thus, the cerebrospinal fluid works as a shock absorber system of the central nervous system, because the central nervous system is immersed in the fluid, reducing the risk of cerebrum traumatism, originated from the direct contact with the skull. If the brain parenchyma or the blood vessels grow in volume, the fluid is drained and the intracranial pressure decreases to a certain limit, to regulate the volume in the skull.

Figure 22:
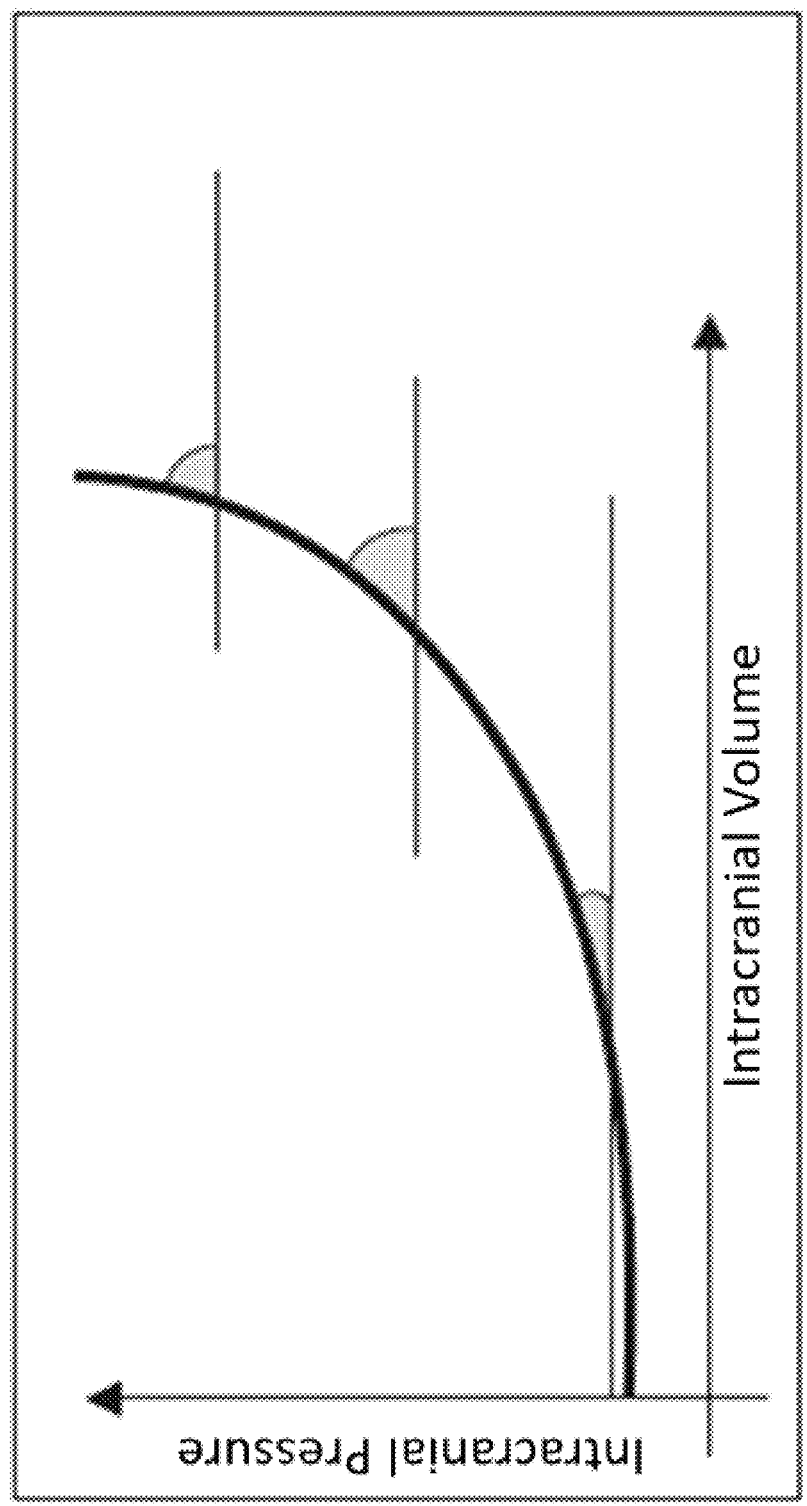
FIG. 22 shows a chart of the Langfitt curve, wherein the y axis represents the intracranial pressure and the x axis represents the intracranial volume.

One of the most important aspects in the cranial cavity from a neurologic perspective is the fact that it is a cavity completely closed, which does not permit a significant volumetric variation, but enough to be detected by the method, system and device proposed by the present invention. The growth of volume by any component is transmitted to the other components, leading to a rise in the intracranial pressure, as shown on FIG. 22, wherein the X axis represents the volume and the Y axis represents the ICP. Tumors, bruises and other intracranial expansive processes compress not only the affected areas, but all the structures in the cranial cavity.

Figure 23:
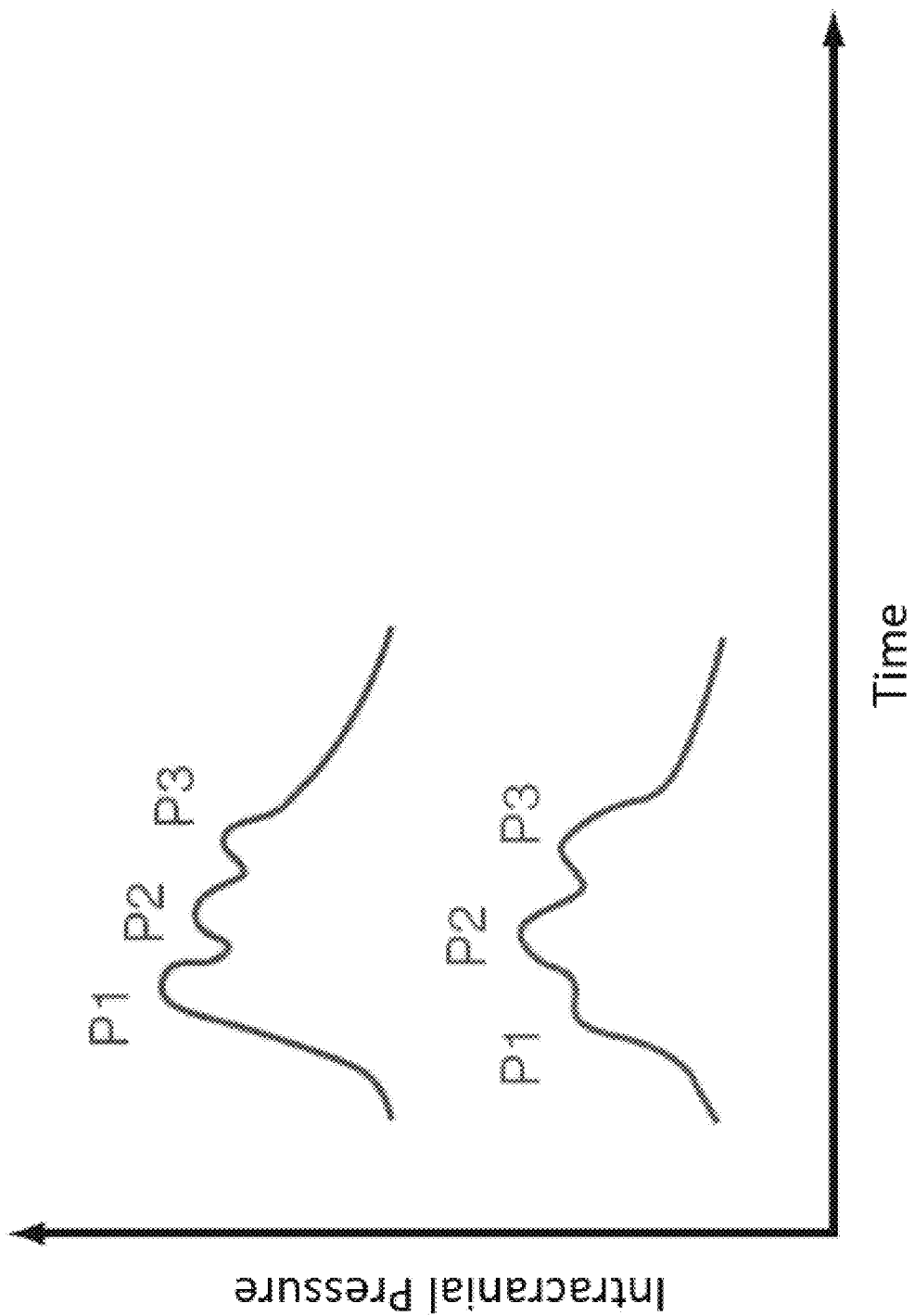
FIG. 23 shows a chart of the intracranial pressure over time, where the upper curve shows a good complacency and the lower curve shows a bad complacency.

A normal ICP curve is shown in FIG. 23, it is a modified arterial pulse and consists of 3 distinctive peaks. P1 is denominated percussion wave, and results from the arterial pressure transmitted from the choroid plexus. P2 is denominated tidal wave, which varies according to a cerebral complacency, and is a reverberation of P1. P3 is denominated dicrotic wave, and precedes the closing of the aortic valve.

Figure 24:
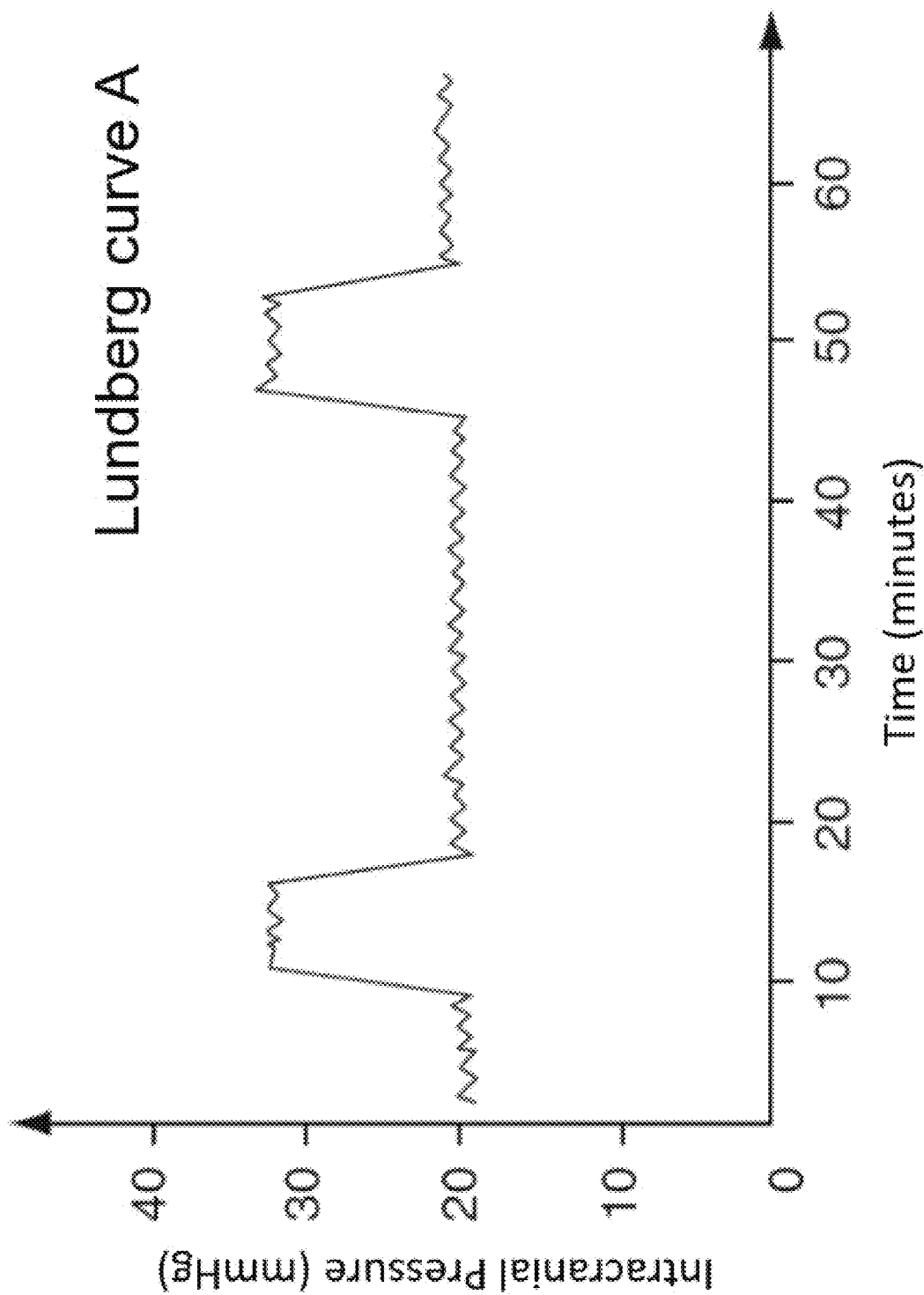
FIG. 24 shows a chart of the Lundberg curve A, plateau, where it is shown intracranial pressure over time.
Figure 25:
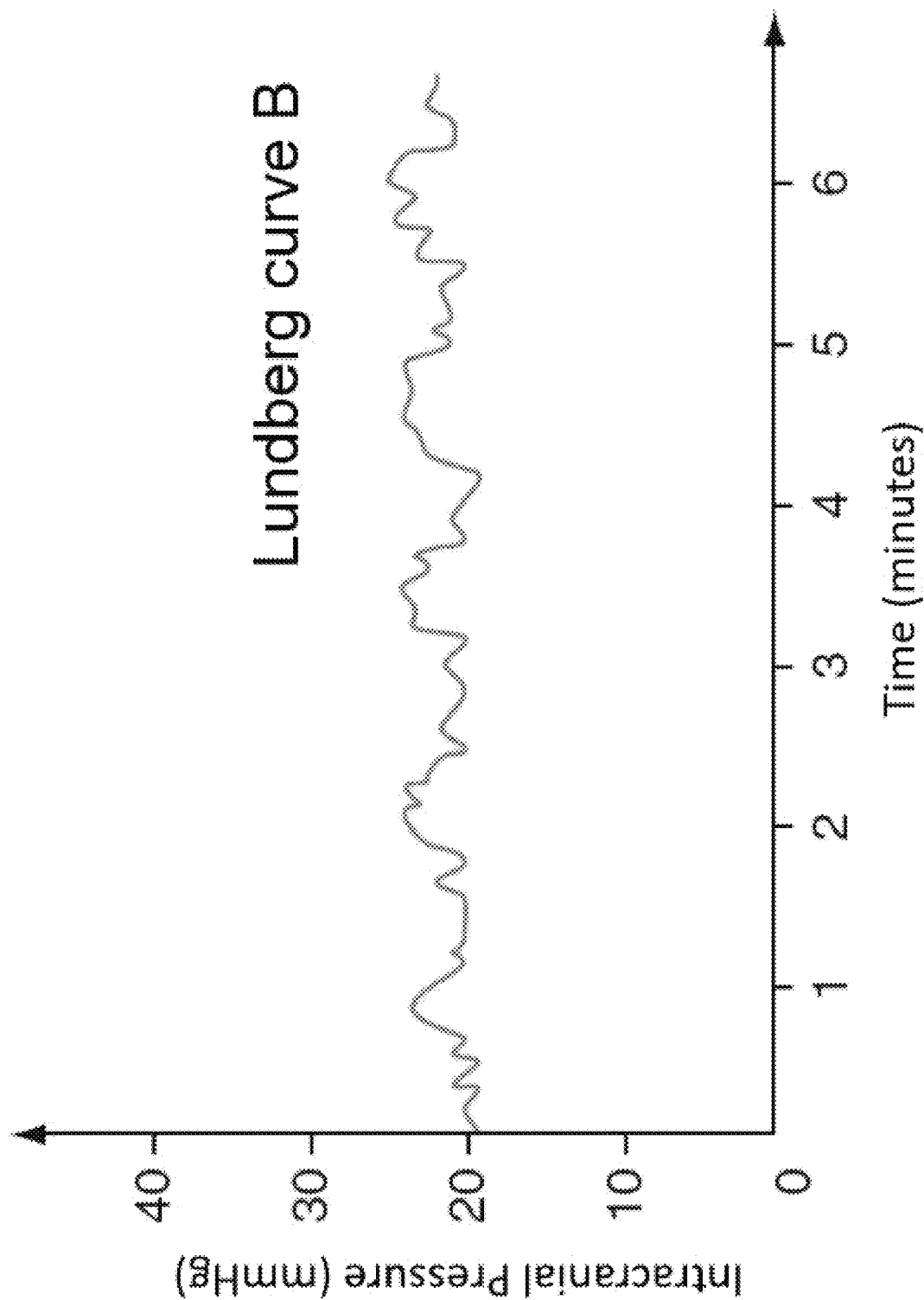
FIG. 25 shows a chart of the Lundberg curve B, pulses, where it is shown intracranial pressure over time.

If the monitoring of the intracranial pressure is being registered over the time, some wave curves can be distinct. The Lundberg waves can be separated in 3 types. As shown in FIG. 24, curve A, plateau, are always pathological, are elevations on the intracranial pressure, of the range of 100 mmHg during 2 to 20 minutes, with the abrupt fall to a basal value, possibly representing a cerebral vasodilatation and are interpreted as grave signals of decompensation of the intracranial pressure. As shown in FIG. 25. Curve B, pulses, occurs from 0.5 to 2 times per minute with amplitude up to 50 mmHg, reflecting a influence of the respiratory cycle on the intracranial pressure. Those signals are seen on normal individuals, but are indicatives of intracranial pathology when the amplitude is above 10 mmHg. Curves A and B are alert signals of a possible complacency injury. Curve C, occurs from 4 to 8 times per minute and relate to arterial curves of Traube-Henring-Meier.

The monitoring of the intracranial pressure is able to measure the pressure, and provide important information about the intracranial dynamic and the complacency of the brain through the analysis of its waveform. The analysis of the intracranial pressure provides information that identifies users with low capacity of adaptability (low complacency) that are susceptible to a raise in the intracranial pressure and a decrease of the cerebral perfusion pressure.

Thus, in one aspect, the present invention provides a method for non-invasive management and monitoring of intracranial pressure, wherein the method comprises the steps of:
  a. detecting analog signals from a user by a detection device;
  b. receiving the detected analog signals on a receiver, each of the signals being related to the intracranial pressure of the user;
  c. processing by a processor the detected analog signals generating processed signals; and
  d. transmitting the processed signals through a transmitter to a pre-configured receiver, wherein the transmitter and the pre-configured receiver are communicating wirelessly.

The term user in the present invention refers to a human or an animal where the system is able to detect the skull volumetric variation.

The step of detecting analog signals from a user comprises a detection of the skull volumetric variation and/or skull deformation, wherein its variation applies a deflection to a pin, said deflection being positive or negative, whereas the transducer of variation (8) is connected to the pin, it deforms the transducer of variation (8), and the transducer of variation (8) generates a differential voltage signal related to the intracranial pressure of the user. This differential voltage signal is received by the receiver and the processing of the signal begins.

In an embodiment, the detected signals from the transducer of variation (8) are directed to the receiver which is communicating to the processor.

The step of receiving the detected analog signal on a receiver comprises the ability to be receptive to any analog signal sent by a detection device, without constricting itself by any method executed by the detection device. In this step, the detected analog signals pass through an electronic circuit that is able to generate electronic information capable to be readable by a processor. In an embodiment, the analog signal received is detected by a pressure sensor, mechanic sensor, inductive sensor, crystal liquid sensor, laser sensor, strain gauge sensor, optic sensor or a combination thereof.

In another embodiment, the receiver comprises the ability to receive a plurality of analog signals, where the receiver is able to receive the signals by serial communication or parallel communication. In an embodiment, the plurality of analog signals, can be, without being restricted to, signals about temperature, environment pressure, humidity, orientation, angular velocity, acceleration, magnetism, and geolocation.

The processing step executed by a processor delimits the type of the processor and which tools are needed in the processing step. The processor comprises at least one tool for processing said analog signals, wherein the tools are described below.

A tool for converting the detected analog signals to digital signals related to the intracranial pressure of the user, without losing the effectiveness of the monitoring of the intracranial pressure. In an embodiment, this tool is an analog to digital converter.

Figure 1:
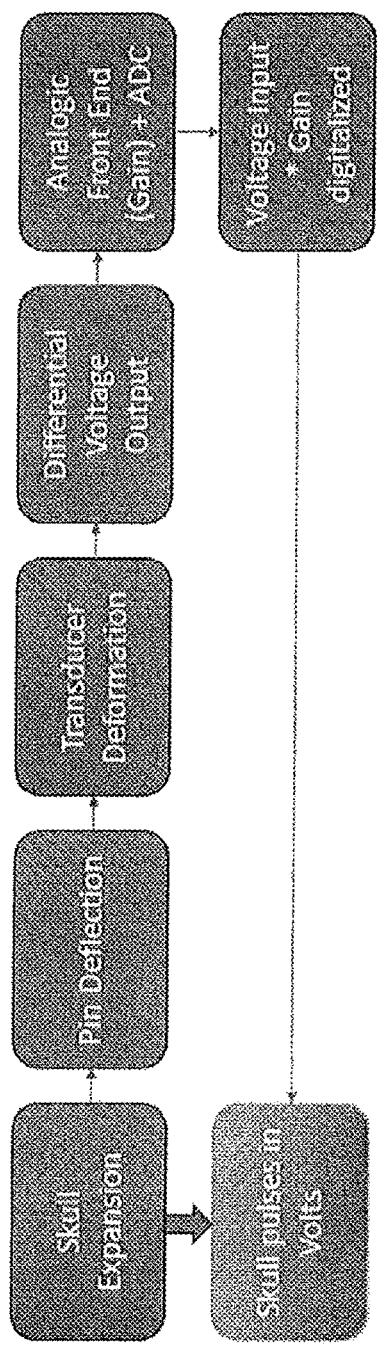
FIG. 1 shows a flow chart of an embodiment of the present invention for non-invasive management and monitoring of a skull volumetric variation, wherein the detected analog signal is processed in order to show the signals of skull volumetric variation in the measurement unit of volts.

In an embodiment, the processor utilizes one of its tools for processing signals related to the intracranial pressure of the user to convert the detected signals into digital signals and amplifies those signals, by using others tools in order to obtain a processed signal to transmit wirelessly by a transmitter, as FIG. 1 shows a converting before the step of further processing by other tools.

A tool for filtering the digital signals for transmitting by the transmitter, wherein this filtering is executed by a firmware to filter most relevant information of the digital signals. In an embodiment, this tool is a filter wherein the filter executes a filtering of digital signals for transmitting by the transmitter.

In an embodiment, the filtering executes a sorting based on events through a tool protocol based on events, wherein the firmware identifies a variation on the most relevant information of the digital signals, and transmits the processed signals.

In one example embodiment, analog signals from the detection device are converted to digital signals using an analog-to-digital converter, for example with 32 bits of resolution. Once the detection device has been properly placed upon the patient, changes in the measurements are expected in only a subset of the bits (e.g., 12 least significant bits). To improve wireless communication, the firmware operates to transmit the most relevant information (i.e., the subset of least significant bits) while filtering out less relevant information (e.g., the remaining more significant bits).

During initial device setup, the firmware analyzes the entire digital signal to identify triggering events. Detecting proper placement of the detection device on the patient is one example event. During initial device setup, the detection device is being moved and the digital signals will experience significant amplitude changes; whereas, once the detection device is properly placed on the patient, the digital signal will experience considerably less amplitude changes, especially in the most significant bits of the digital signals. By comparing the most significant bits of the digital signals to a predetermined threshold, the firmware can identify when the detection device has been properly place on the patient. That is, the detection device is deemed to be properly place on the patient when the variation in amplitude of the most significant bits are less than the predetermined threshold. Additionally or alternatively, the detection device may use input from an integrated motion sensor (e.g., an accelerometer) to determine when the detection device has been properly place on the patient.

Upon detecting proper placement of the detection device on the patient, the firmware may initial transmit the entire measurement signal (i.e., all 32 bits) to the receiver and subsequently transmit only a subset of the bits (i.e., 12 least significant bits) to the receiver until detection of another triggering event (e.g., removal of the detection device). The receiver in turn can reconstruct the full scale of the date without loss of information. In this way, less data is sent and wireless communication between the transmitter and the receiver is improved. Other types of sorting and filtering of the measurement data is contemplated by this disclosure.

In another embodiment, the filtering executes a dynamic sorting through a tool dynamic protocol, wherein the firmware sorts out the most relevant information and the least relevant information from the digital signals, and transmits the processed signals. In another embodiment, the filtering executes a tool combination protocol wherein the combination protocol comprises at least a combination of the previously mentioned protocols.

A tool for converting the digital signals into digital signals of volumetric variation, wherein the unit of measurement of the processed signals are in meter and its variations, e.g., micrometers, centimeters, nanometers, etc. In an embodiment, this tool is a converter wherein the converter converts the digital signals into digital signals of volumetric variation in the range of micrometers.

Figure 2:
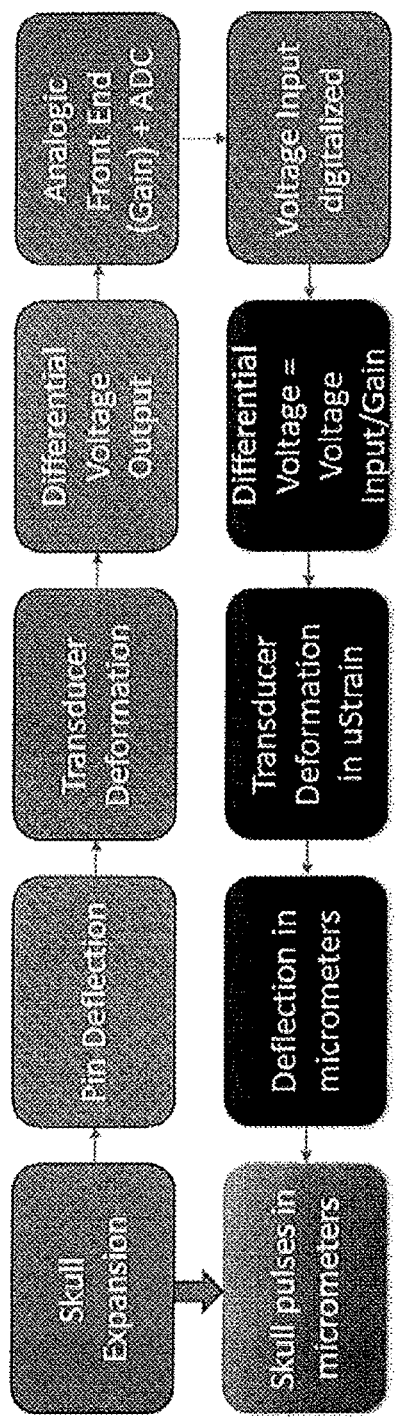
FIG. 2 shows a flow chart of another embodiment of the present invention for non-invasive management and monitoring of a skull volumetric variation, wherein the detected analog signal is further processed in order to show the signals of skull volumetric variation in the measurement unit of micrometers.

In an embodiment, the detected analog signals are converted in digital signals, then converted by the tool of converting the digital signals into digital signals of volumetric variation, wherein the processed signals comprises at least a measurement describing the displacement of the skull volumetric variation, as shown in FIG. 2.

A tool for modulating digital signals, digital signals of volumetric variation or analog signals for transmitting by the transmitter. In an embodiment, there are different tools of modulating for each of the different types of signals. In another embodiment, this tool is a modulating unit, wherein the modulating unit modulates at least one of the different types of signals.

In a further embodiment, the processor modulates those digital signals for transmitting by the transmitter, where in the modulated signals are the processed signals to be received by a pre-configured receiver.

In another embodiment, the processor modulates the received analog signals for transmitting by the transmitter, where in the modulated signals are the processed signals to be received by a pre-configured receiver.

The modulation of digital signal comprises at least modifying the incoming digital signal to transfer the digital signal in order to enable a wireless communication of a transmitter and a communication channel, e.g., a receiver, a pre-configure receiver, a network comprising a bandpass filter, etc.

The modulation of analog signal consists of at least modifying the incoming analog signal to transfer the analog signal at a different frequency, phase, amplitude, quadrature or angle in order to enable a wireless communication of a transmitter and a communication channel.

Figure 3:
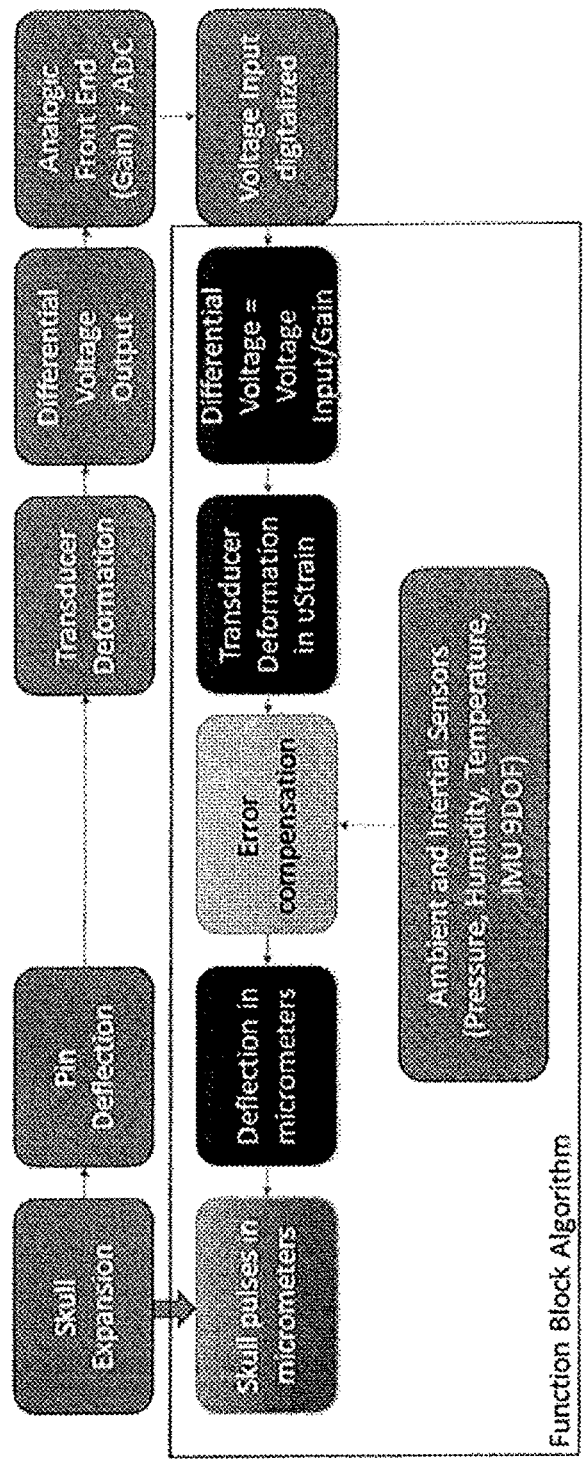
FIG. 3 shows a flow chart of another embodiment of the present invention for non-invasive management and monitoring of a skull volumetric variation, wherein a plurality of detected analog signal are processed in order to show the signals of skull volumetric variation in the measurement unit of micrometers and to remove environment noises in the analog signal related to the ICP of the user.
Figure 4:
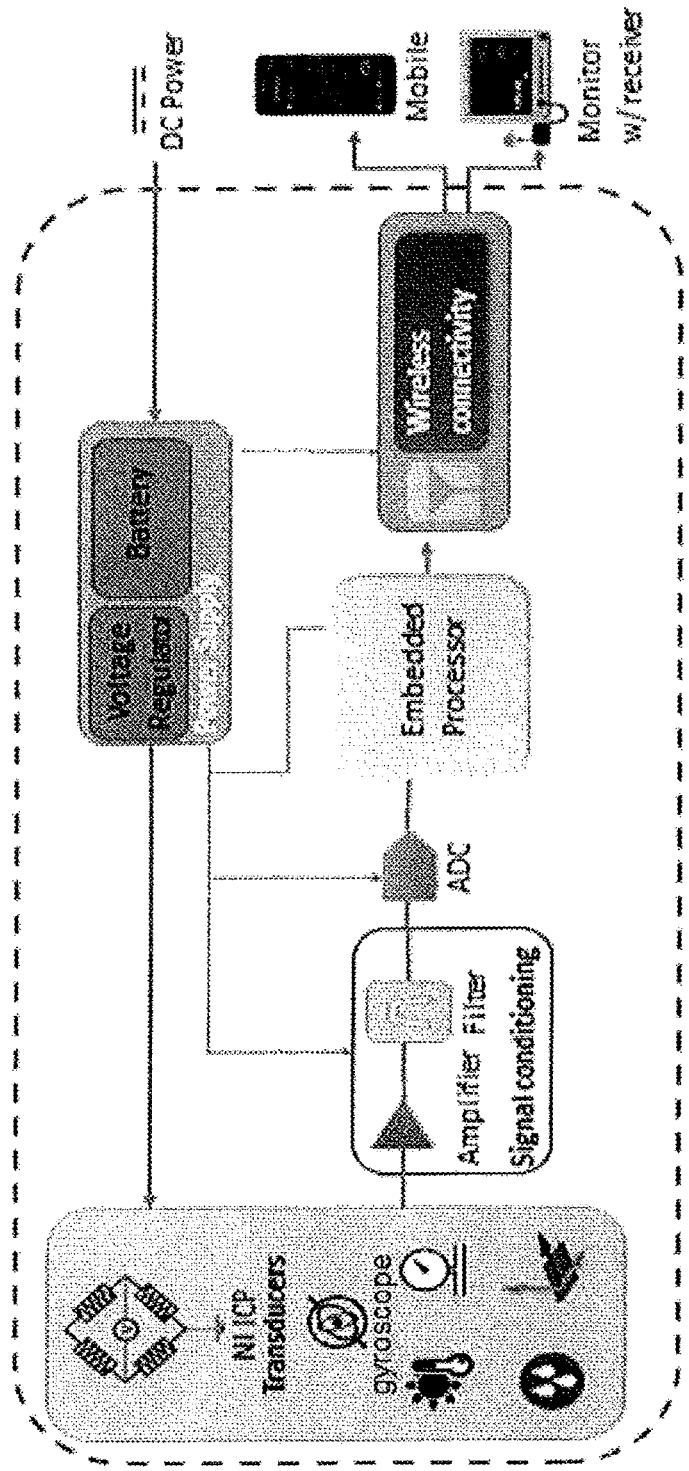
FIG. 4 shows a schematic diagram of one of the embodiments of the system showing a performance of the system.

A tool for compensation signal, wherein the processor detects signals provided by at least one correction sensor. In an embodiment, after the detection of the signals provided by at least one correction sensor the processor process the compensating signal and regulates the digital signals originated from the detection device, generating a compensated digital signal related to the intracranial pressure of the user, as shown in FIG. 3. In an embodiment, this tool is a compensatory unit for the detection of the compensation signal.

The correction sensor is any device capable of detecting signals that relate to physiological parameters of a user, wherein that signal may interfere in the intracranial pressure measurement, or detecting signals that relate to the functionality of the detection device. In an embodiment, the correction sensor is an environment sensor, wherein the environment sensor comprises at least a temperature sensor, or a barometer, or a hygrometer.

In another embodiment, the correction sensor is a motion sensor, wherein the motion sensor comprises at least a gyroscope, or an accelerometer, or a magnetometer. In another embodiment, the correction sensor is a global positioning system for geolocation. In another embodiment, the correction sensor is at least a motion sensor, an environment sensor, a global positioning system, or a combination thereof.

In an embodiment, the signals detected by at least one correction sensor, when processed by the tool for compensation signal remove noises and interferences on the signal detected by the detection device, e.g., when the user change the initial position that started the monitoring the tool for compensation signal utilizes the signals detected by at least one correction sensor to remove the noises and interferences that this change may cause.

In the step of transmitting the processed signals through a transmitter to a pre-configured receiver, the processed signal is transferred from the transmitter to the pre-configured receiver through signals containing the information related to the intracranial pressure of a user. In an embodiment, the wireless communication between the transmitter and the pre-configured receiver is a near field communication. In another embodiment, the wireless communication between the transmitter and the pre-configured receiver is a radio frequency identification. In another embodiment, the transmitter is communicated with the pre-configured receiver by Bluetooth® standard protocol.

In an embodiment, the present method executes all steps of detecting analog signals, receiving, processing and transmitting these signals in real time, wherein these steps are executed uninterruptedly.

In a second aspect, the present invention provides a system for non-invasive management and monitoring of intracranial pressure, wherein the system comprises:
   a. a detection device for detecting analog signals from a skull volumetric variation;
   b. a receiver communicating with the detection device and receiving analog signals related to the intracranial pressure of a user;
   c. a processor comprising at least a tool for processing signals related to the intracranial pressure of the user, wherein the processor is communicating with the receiver; and
   d. a transmitter, wherein the transmitter is communicating with the processor and comprising a module to transmit processed signals wirelessly.

In an embodiment, the system further comprises at least one pre-configured receiver. The pre-configured receiver is any receiver that communicates with the transmitter, the pre-configured receiver being configured to communicate with at least one electronic device to insert the received processed signals into the electronic device to a further processing of the processed signal and sending said signal to a cloud server.

The system further comprises a headpiece for accommodating at least one device around the head of the user. In an embodiment, the headpiece is a strip for accommodating at least a device around the head of the user comprising a fastener, the fastener adjusting the strip on the head of the user. In a further embodiment, the strip is flexible and accommodates itself around the head of the user.

In an embodiment, the detection device is a device for measuring of a skull volumetric variation.

In a third aspect, the present invention provides a device for measuring a skull volumetric variation comprising:
   a. a transducer of variation (8) comprising a detector of variation provided with a first end configured to receive a deflection related to skull volumetric variation, wherein the transducer of variation (8) converts a detected variation on electric signal; and
   b. a housing, wherein the transducer of variation (8) is positioned inside the housing.

The detector of variation is any object capable of transferring the energy detected from the skull volumetric variation to the transducer of variation (8). In an embodiment, the detector of variation comprises a pin, in which said pin is connected to the transducer of variation (8), wherein the pin detects variation and generates a deformation on said transducer of variation (8) for converting on electric signal.

In an embodiment, the transducer of variation (8) comprises a electric circuit connected to a flexible material, wherein the deformation of the flexible material is detected by the electric circuit.

The housing is any material or set of materials disposed in a design to protect the transducer of variation (8) and capable of accommodating said transducer of variation (8). In an embodiment, the housing comprises at least one enclosure part around the detector of variation, wherein the enclosure part protects the detector of variation from unnecessary movements.

In a further embodiment, the enclosure part is positioned around the detector of variation, the enclosure part stops the detector of variation movement when the device is turned off and delimits the maximum deformation the transducer of variation (8) can achieve.

Enclosure part is any material inside the housing that prevents the erroneous movement of the transducer of variation (8), and provides protection against direct impact.

In an embodiment, the housing comprises a switch (5), a delimiting enclosure (6) and a locking device (7), wherein the locking device (7) comprise fixation of the pin when the power is off in order to protect the device and when the power is off the delimiting enclosure (6) delimits the deformation of the transducer of variation (8).

EXAMPLE

The examples shown here are intended only to illustrate one of several ways of implement this invention, however, without limiting the scope thereof.

The system for monitoring and managing the intracranial pressure, is non-invasive and its objective is to be simple and easy to use, resistant and efficient. The system comprises: low energy architecture, defibrillation protection, built-in patient isolation, front end biosensing circuit for non-invasive transducer of variation (8), configurable rgb led for specifics indicators, low energy power management, long battery life with li-ion battery through an internal battery (9) and an external battery (15), internal fault monitors, advanced encryption standard hardware, powered by an embedded processor arm cortex m4f comprising digital signal processor, single instruction, multiple data, tools for processing signals related to the intracranial pressure of the user, such as:

Analog to digital converter, high-accuracy and resolution architecture with differential input, autogain, auto offset, low temperature, offset and gain drifts.

Compensatory unit comprising internal temperature sensor, environment sensors such as temperature sensor, humidity sensor, pressure sensor, motion sensors such as accelerometer, gyroscope, magnetometer, gps for geolocation.

Digital signals processing instructions, floating point unit (FPU), single-cycle multiply and accumulate, hardware division for energy-efficient process of computationally complex operations.

A firmware that executes all functions projected by the hardware. Based on the low power profile, the firmware has all modus operandi seeking an efficient energy cost. All accesses are optimized to use less energy. The non-volatile memory of the hardware contains all information necessary for the device to be paired automatically.

In an embodiment, the firmware filters those digital signals wherein the filtering utilizes a tool protocol based on events, wherein the firmware comprises a variation detector of the most relevant information of the digital signals. Through the variation detector the firmware filters signals based on the change of the most relevant information.

In another embodiment, the firmware filters those digital signals wherein the filtering utilizes a tool dynamic protocol, wherein the firmware comprises a sorter device that sorts out the most relevant information and the least relevant information from the digital signals.

In another embodiment, the firmware filters those digital signals wherein the filtering utilizes a combination of the protocols mentioned. In a further embodiment, the processor converts the digital signals into digital signals of volumetric variation, wherein the digital signals of volumetric variation are measures in the range of micrometers.

The long battery life with li-ion battery through an internal battery (9) and an external battery (15) energizes the system, wherein the external battery (15) is a first power supply for the system and recharges said internal battery (9), when the external battery is recharging via usb with fuel gauge the internal battery (9) serves the purpose of a second power supply for the system. The system is further comprises The system further comprises for transmission of data: wireless connectivity through a wireless antenna (13), Bluetooth® 5.0, on-chip near field communication tag, a pre-configured receiver, secured authenticated pairing between two pre-configured devices, central process unit, high throughput, advertising extensions, Bluetooth low energy (BLE), u.fl connector for external omnidirectional antenna.

In an embodiment, the system has high priority in the steps of receiving, processing and transmission of signals to a pre-configured receiver connected to a central processing unit. The transmission of data being fluid, in real time, without losing relevant data and with cryptography of the data for preventing interceptions of the collected signals.

The firmware update is executed through an app over the air. The system is initially configured with a bootloader, allowing the maintenance and repair of firmware.

The pre-configured receiver is responsible for reconstructing the analog signal related to intracranial pressure, collected through the pre-configured receiver, and to deliver its signal to a monitor, app or a central processing unit.

In an embodiment, the system comprises a database with rules, function, and pre-described methods implemented to ease the access to read and inputting of new configuration of tools. Tools such as the analog to digital converter, with serial peripheral interface communication, has a diverse array of configurations of filters, sample rates, auto gain and auto offset. Those tools can be accessed through a reading mode and execute the processing through a writing mode, allowing remote dynamic configuration.

Figure 5:
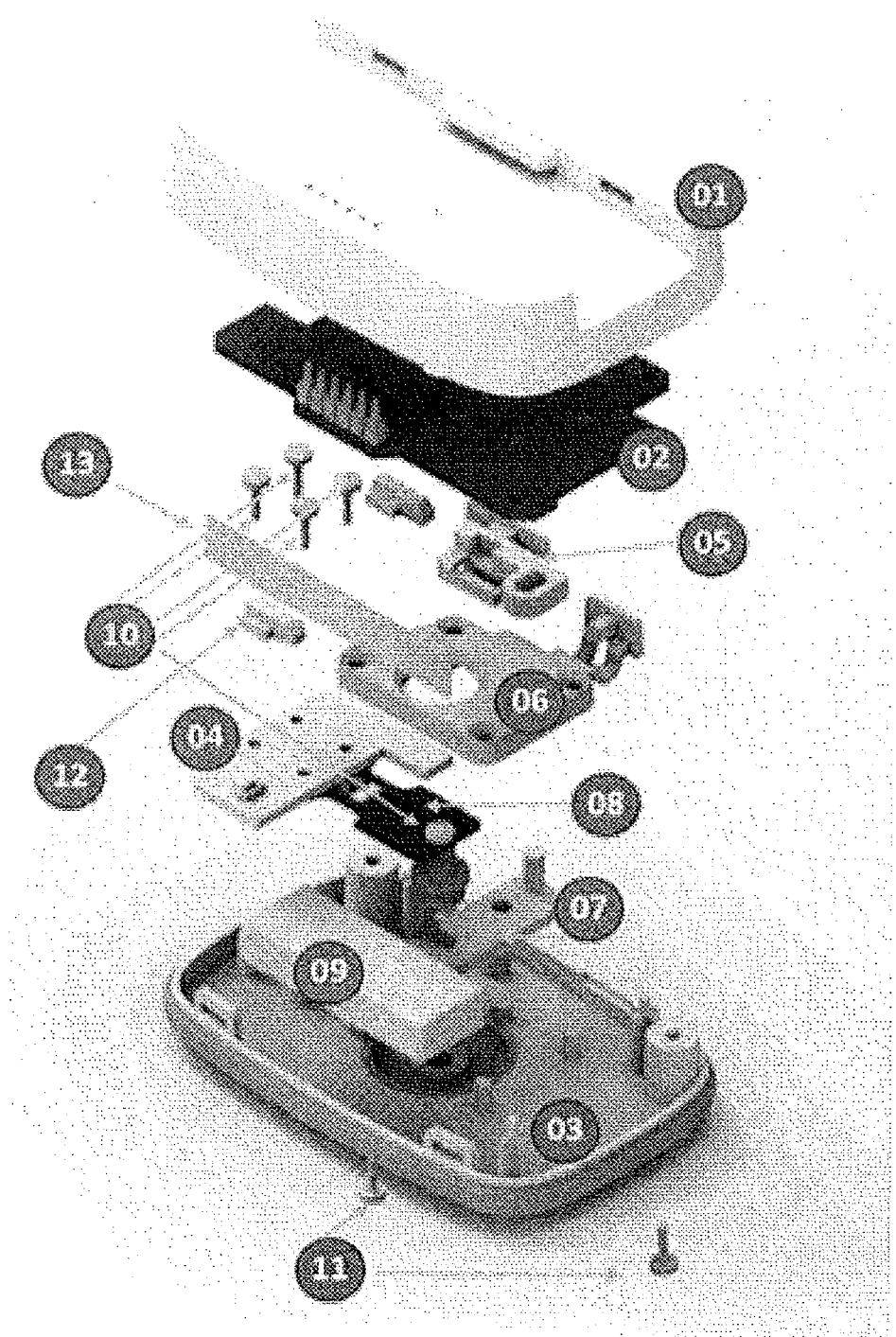
Figure 6:
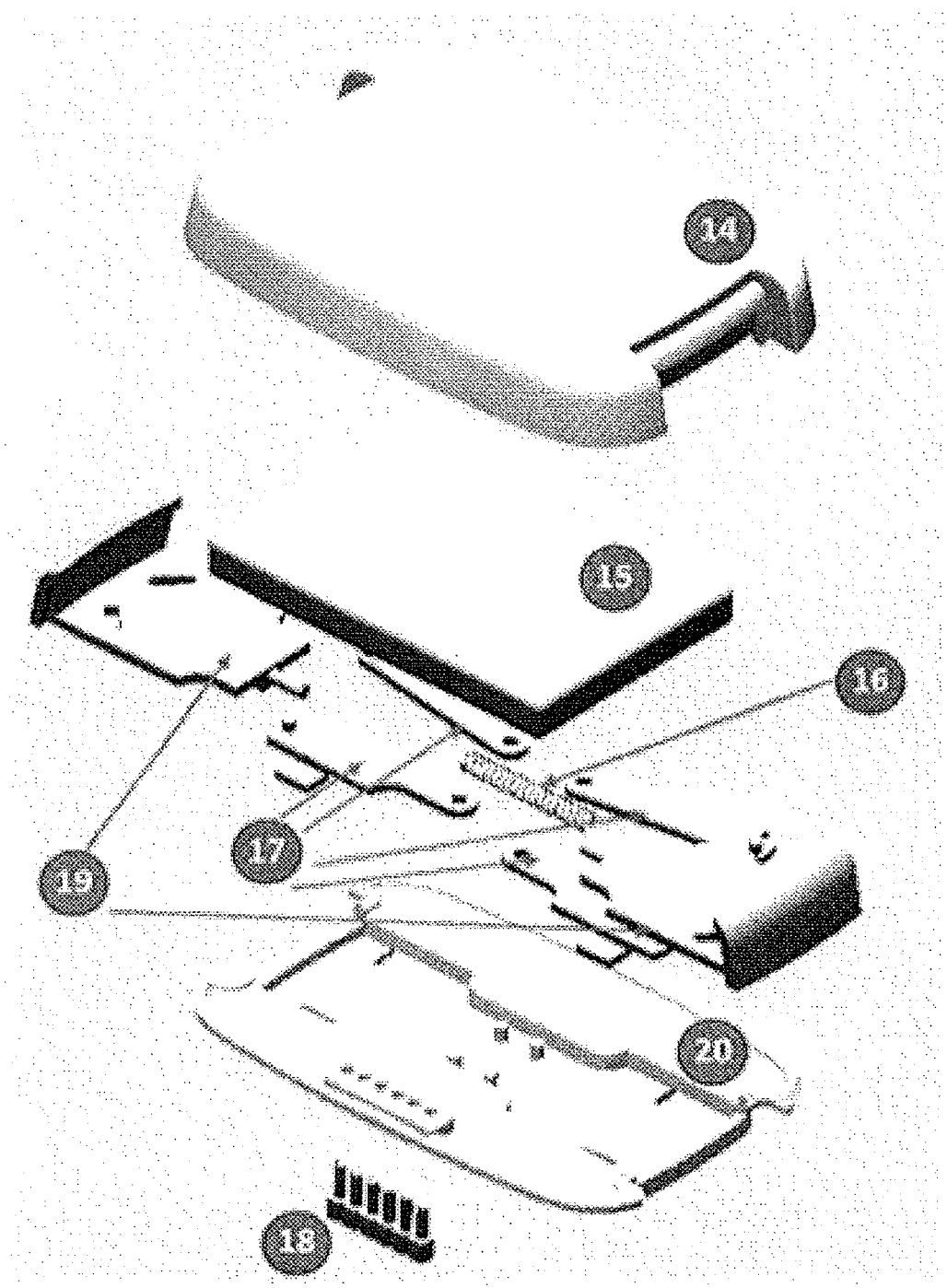
Figure 7:
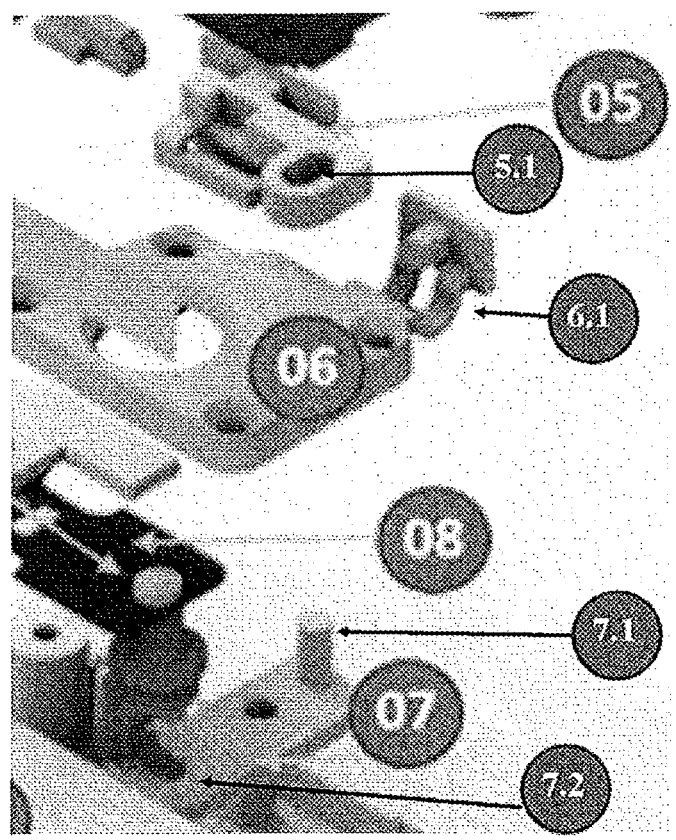
Figure 8:
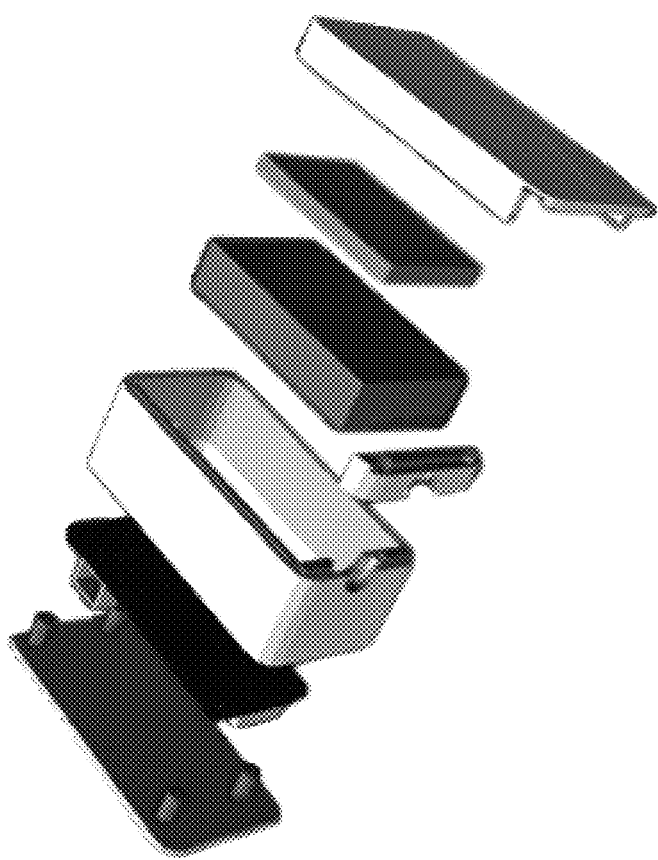
FIG. 8 shows an embodiment of device for measuring a skull volumetric variation.
Figure 9:
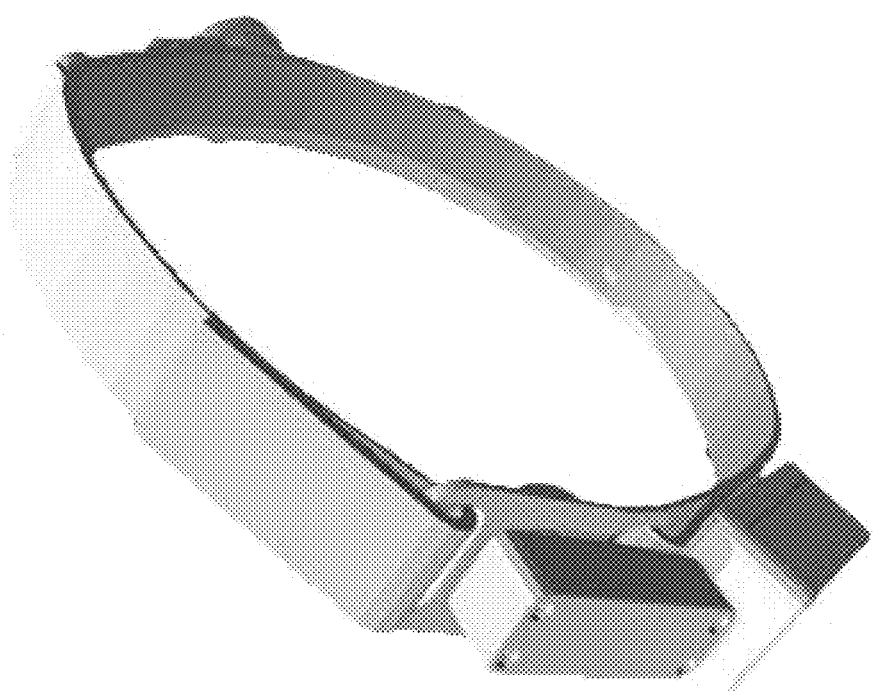
FIGS. 9 to 12 shows views of an embodiment of the system for non-invasive management and monitoring of a skull volumetric variation.
Figure 10:
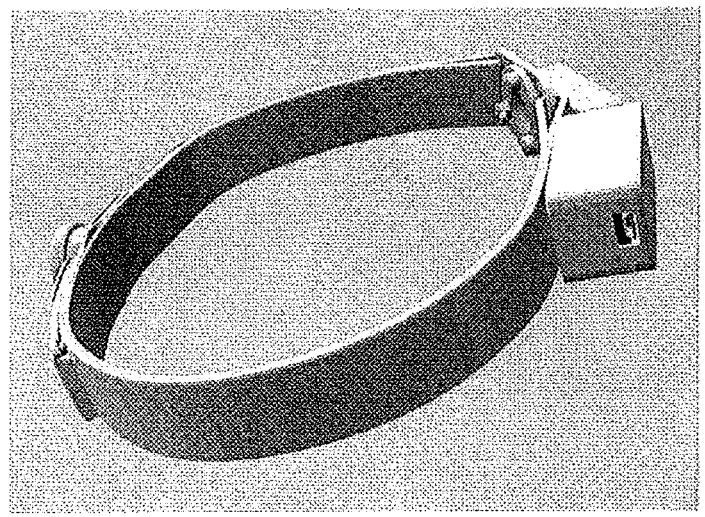
Figure 11:
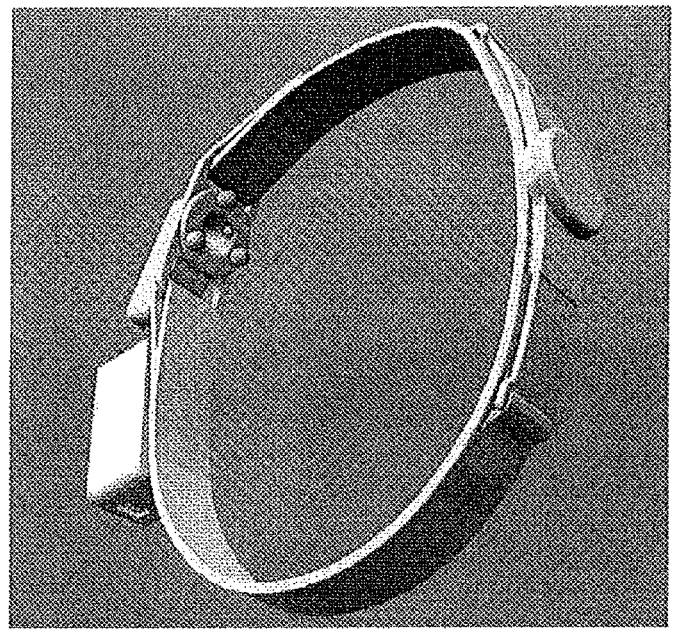
Figure 12:
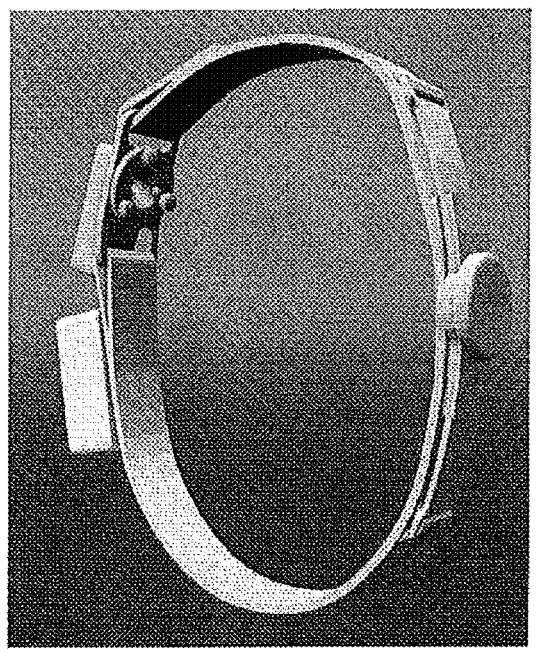
Figure 13:
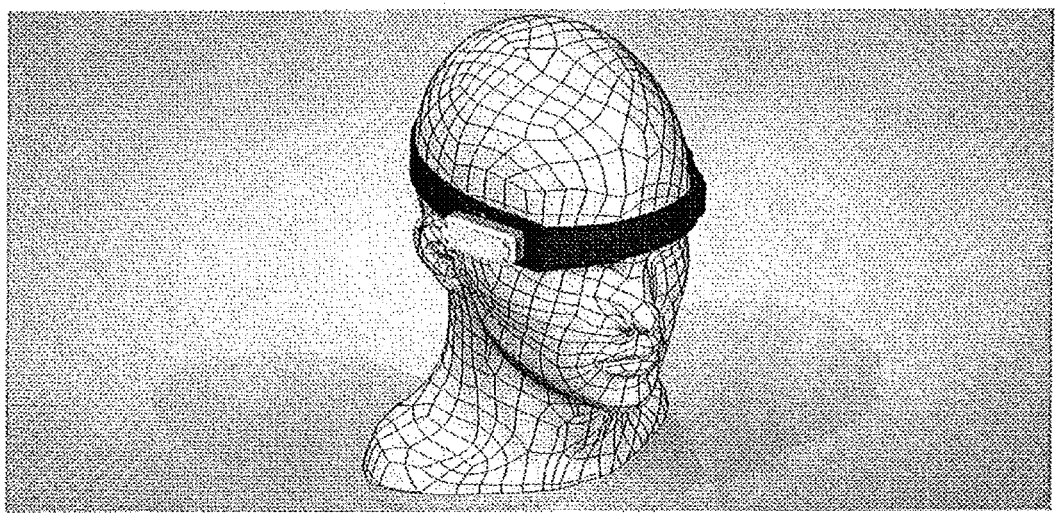
FIGS. 13 to 17 shows views of an embodiment of the system for non-invasive management and monitoring of a skull volumetric variation positioned around the head of a user.
Figure 14:
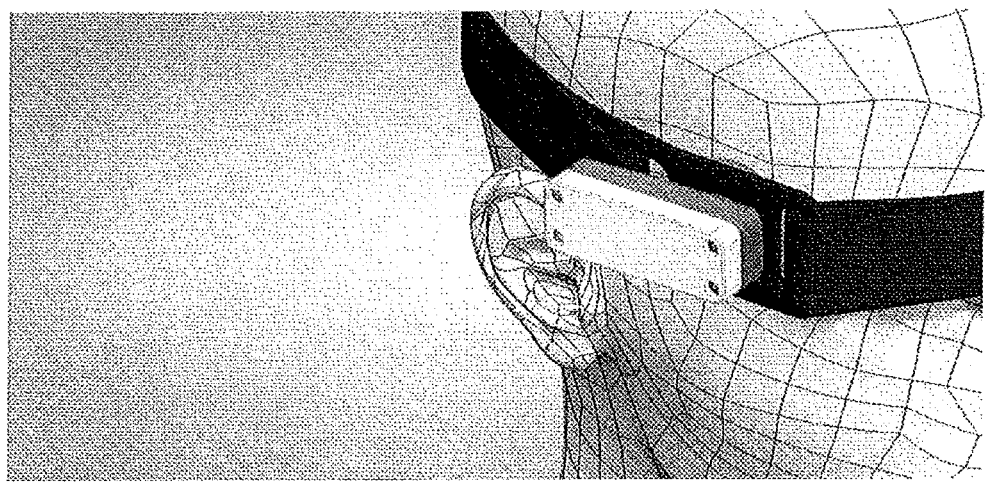
Figure 15:
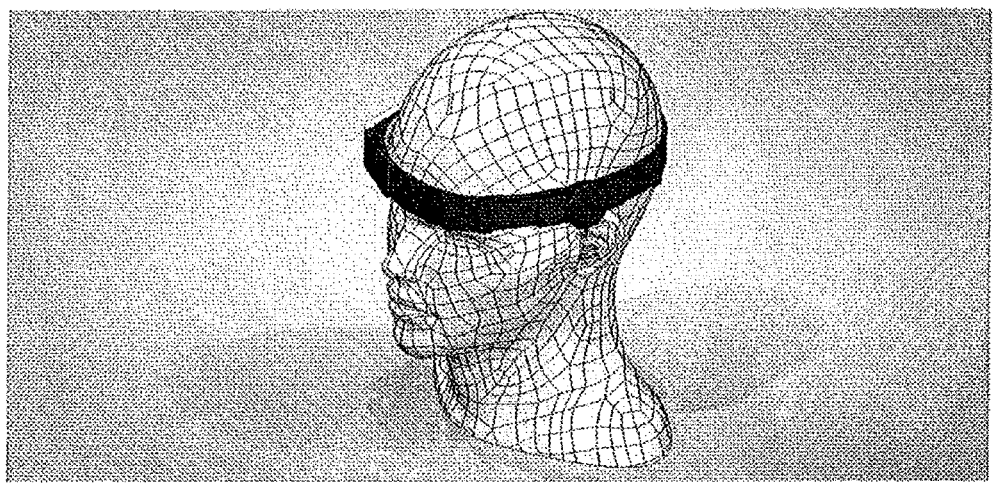
Figure 16:
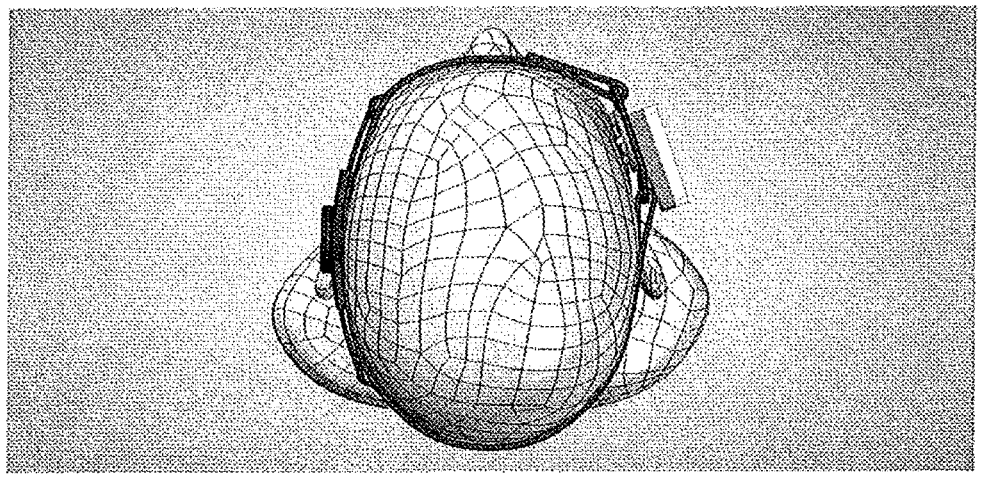
Figure 17:
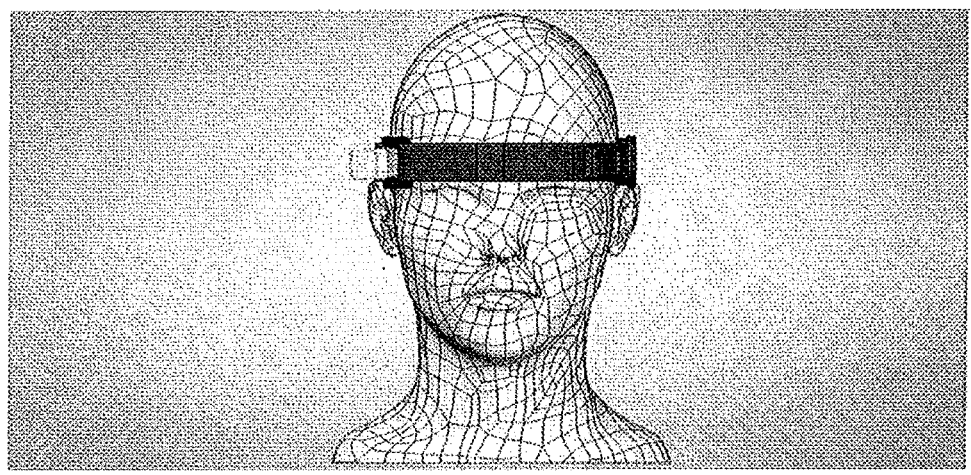
Figure 18:
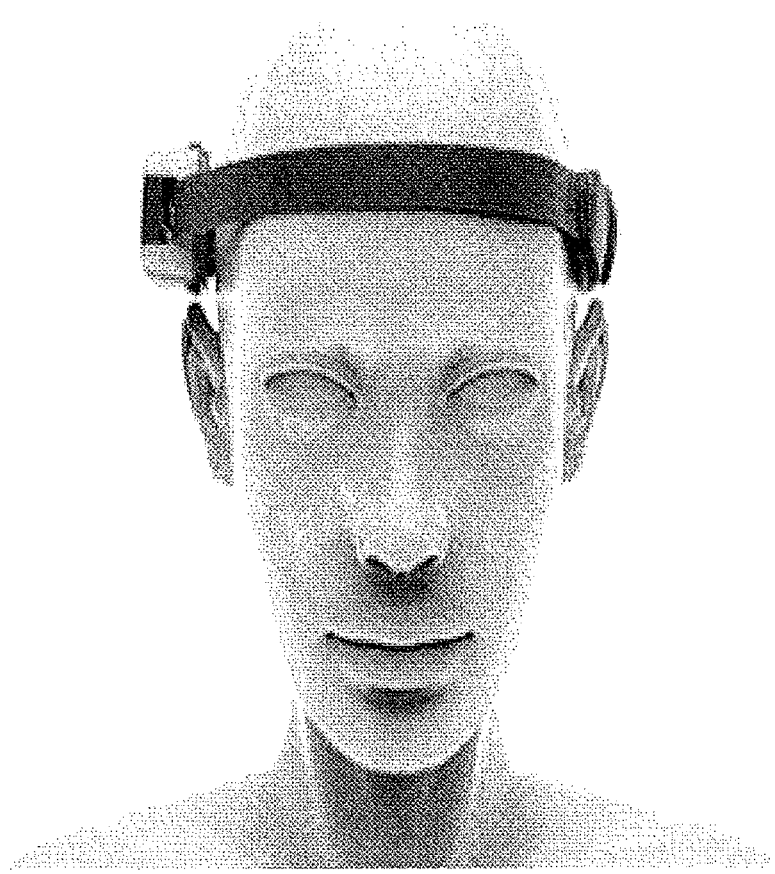
FIGS. 18 to 20 shows views of another embodiment of the system for non-invasive management and monitoring of a skull volumetric variation positioned around the head of a user.
Figure 19:
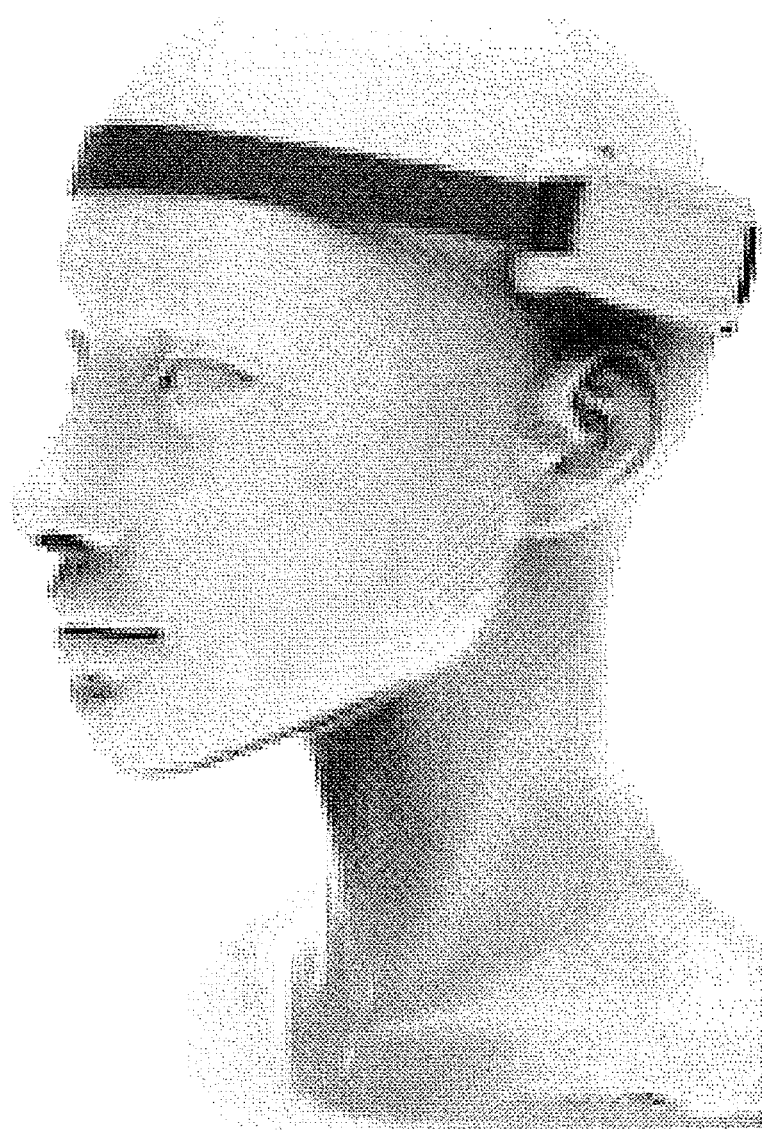
Figure 20:
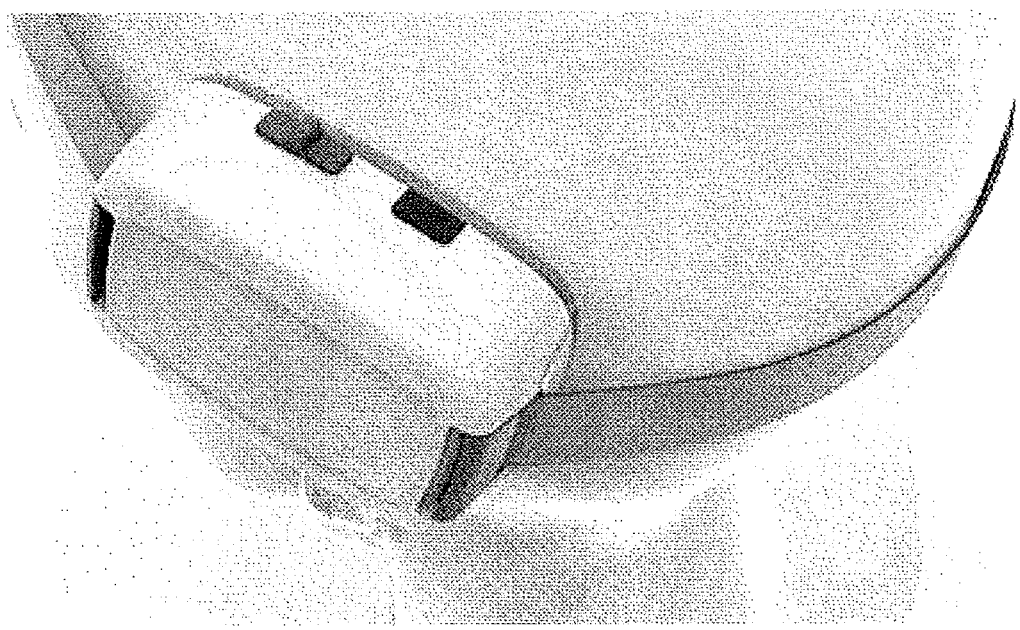

For a further explanation of the embodiment, the device is shown in FIG. 5. In an embodiment the housing comprises the upper protection (1) connected to the lower base (3), in order to envelop the components and protect them, wherein the lower base connects to the skin of the user when in utilization of the device.

In this embodiment, the processor comprising tools for processing signals is the circuit board of the main sensor (2) and communicates with the transducer of variation (8), wherein one of the auxiliary screws (10) works as the detector of variation of the device. The transducer of variation (8) is cantilevered fixed on a base (4), wherein this base also contains a circuit board of the at least one correction sensor positioned at the base (4) working as a compensatory unit connected through auxiliary screws (10) to the housing, receives the analog signals from the correction sensors and communicates with the circuit board of the main sensor (2), in order to process with better precision the intracranial pressure or in order to transmits received analog signals from the at least one correction sensor.

In an embodiment, the locking device is provided with a first end comprising a trigger (7.1) and a second end, opposite to the first end, comprising an opening (7.2), wherein the opening (7.2) is adapted to be associated to the detector of variation. In an embodiment, the opening (7.2) connects to the pin, wherein the pin has a gap to connect the opening (7.2) between two raised peaks around it in order to stop the movement perpendicular to the connection of the opening (7.2) and the pin. In an embodiment, the opening (7.2) connects to the pin, wherein the pin has a gap to connect the opening (7.2) above a raised peak in order to stop the movement of the pin capable of deforming the transducer of variation (8). In an embodiment, the opening (7.2) connects to the pin, wherein the pin and the opening have circular perimeters, such pin having a bigger diameter than the opening (7.2) and when connected the friction interferes in the movement perpendicular to the connection of the opening (7.2) and the pin.

In an embodiment, the delimiting enclosure (6) is positioned opposite to the first end of the detector of variation, and the delimiting enclosure (6) comprising a limiting element (6.1). In further embodiment, the housing comprises a safety space between the delimiting enclosure (6) and the transducer of variation (8), wherein the safety space provides a safe deformation of the transducer of variation (8).

an embodiment, the switch (5) comprises a trigger opening (5.1) configured to be associated with the trigger (7.1), wherein the trigger (7.1) is positioned inside the trigger opening (5.1) and said switch (5) comprises a displacement limited by the limiting element (6.1).

The internal battery (9) is inside the housing. The screws (11) fasten the system to ensure every component is connected and the support part (12) is above the circuit board of the at least one correction sensor positioned at the base (4). The wireless antenna (13) works as the transmitter of the system, is positioned inside the housing, communicating with the circuit board of the main sensor (2) and transmits the processed signals to a pre-configured receiver.

The external protection (14) covers the upper protection (1) for protecting alongside the upper protection (1), an external battery (15) connected to the upper protection (1). A spring (16) connected to interlinked enclosures (19) and in combination with bond enclosures (17) are able to lock and unlock the external battery (15) on the housing. The battery connectors (18) fixed on the circuit board of the main sensor (2) enable the communication of the external battery (9) to the circuit board of the main sensor (2). The under protection (20) positioned between the circuit board of the main sensor (2) and the upper protection (1) protects the circuit board of the main sensor (2) from direct impact.

In another exemplary embodiment, the method is executed as shown in FIG. 1, the skull volumetric variation of the user applies a deflection to a pin of the detection device. The pin transfers the deflection in order to deform a transducer of variation generating a differential voltage signal related to the intracranial pressure of the user.

This signal is analog and received by a receiver, then directed to a processor for a conversion of the analog signal into a digital signal. In this example, the processor utilizes an ADC tool for this conversion. The digital signal is modulated generating a processed signal ready to be transmitted by a transmitter. The transmitter transmits the processed signal to a pre-configured receiver wirelessly.

In another exemplary embodiment, the method is executed as show in FIG. 2, the skull volumetric variation of the user applies a deflection to a pin of the detection device. The pin transfers the deflection in order to deform a transducer of variation generating a differential voltage signal related to the intracranial pressure of the user.

This signal is analog and received by a receiver, then directed to a processor for a conversion of the analog signal into a digital signal and to amplify said digital signal. In this example, the processor utilizes an ADC tool for this conversion. Then the processor executes another tool, converting the digital signals into digital signals of volumetric variation in the range of micrometers. The digital signals of volumetric variation are modulated to be transmitted by a transmitter. The transmitter then transmits the digital signals of volumetric variation to a pre-configured receiver wirelessly.

In another exemplary embodiment, the method is executed as show in FIG. 3. The skull volumetric variation of the user applies a deflection to a pin of the detection device. The pin transfers the deflection in order to deform a transducer of variation generating a differential voltage signal related to the intracranial pressure of the user.

In parallel to the detection of skull volumetric variation, a plurality of environment and inertial sensor detects pressure, humidity, temperature, acceleration, geolocation and magnetism and send those signals to the processor.

The differential voltage signal is analog and received by a receiver, then directed to a processor for a conversion of the analog signal into a digital signal and to amplify said digital signal. The processor further process the digital signal utilizing a converter tool for converting the digital signals into digital signal of volumetric variation in the range of micrometers. A compensatory unit tool of the processor then processes the digital signal of volumetric variation and the signals detected by the plurality of environment and inertial sensor generating a compensating signal, which eliminates the noises from the movement of the user or other decompensation on the monitoring of the user, e.g., a user under the sun moves to a place with roof the processing of signals detects the variation on temperature controlling the physical variation this change of temperature may cause. The compensating signal is modulated to be transmitted by a transmitter. The transmitter then transmits the compensating signal to a pre-configured receiver wirelessly.

Those well versed in the art will value the knowledge here, and may reproduce the invention in the manner provided and other variants, covered within the scope of appended claims.

What is claimed is:

1. A method for non-invasive management and monitoring of intracranial pressure, wherein the method comprises the steps of:
   a. detecting an analog signal from a user by a detection device comprising a transducer of variation, an environmental sensor comprising a temperature sensor, and at least one of a gyroscope and an accelerometer configured to be positioned on the user's head and performs a detection of a skull volumetric variation, wherein the skull volumetric variation is positive or negative and causes a displacement on the transducer of variation;
   b. receiving the detected analog signal on a receiver, wherein the detected analog signal represents measurements of skull volumetric variation;
   c. processing, by a processor, the detected analog signal by converting the detected analog signal to a digital signal and identifying a trigger event from the digital signal, wherein an individual measurement in the detected analog signal is represented by a sequence of bits in the digital signal;
   d. upon identifying the trigger event, transmitting, by a transmitter, the entire sequence of bits for a given measurement in the digital signal to a pre-configured receiver, wherein the transmitter and pre-configured receiver are communicating wirelessly;
   e. transmitting, by the transmitter, only a subset of least significant bits from a sequence of bits for subsequent measurements in the digital signal until another triggering event is identified.

2. The method according to claim 1, further comprises converting digital signals into digital signals of skull volumetric variation, wherein the converting of the digital signals comprises at least a measurement describing a displacement of the skull volumetric variation.

3. The method as claimed in claim 1, wherein the transducer of variation includes a pin configured to deflect in response to skull volumetric variation and the transducer of variation generates a differential voltage signal related to the intracranial pressure of the user in response to pin deflection.

4. The method as claimed in claim 1, wherein the steps are executed in real time.

5. The method according to claim 1, wherein the processor additionally comprises a tool of compensating signal for regulating the digital signals related to the intracranial pressure of the user and generating a compensated digital signal related to the intracranial pressure of the user, wherein the regulating is based on detected signals provided by at least one correction sensor, the at least one correction sensor being a temperature sensor.

6. The method according to claim 5, wherein the processor additionally comprises a correction sensor being a motion sensor, wherein the tool of compensating signal eliminates noises, related to a movement of the user, from the digital signal related to the intracranial pressure of the user.

7. The method according to claim 1, further comprises
   a. comparing, by the processor, most significant bits of the digital signal to a predetermined threshold to identify when the detection device has been properly placed on the user's head; and
   b. initially transmitting, by the transmitter, the entire sequence of bits for the given measurement, and subsequently transmitting only a subset of the least significant bits for subsequent measurements until removal of the detection device.

8. The method according to claim 1, further comprises comparing a subset of most significant bits from the entire sequence of bits to a predetermined threshold to identify an occurrence of the trigger event.

9. A system for non-invasive management and monitoring of intracranial pressure, wherein the system comprises:
   a. a detection device comprising a transducer of variation, an environmental sensor comprising a temperature sensor, and at least one of a gyroscope and an accelerometer configured to be positioned on a user's head for detecting an analog signal from a skull volumetric variation, wherein the skull volumetric variation is positive or negative and causing a displacement on the transducer of variation;
   b. a receiver communicating with the detection device and receiving the detected analog signal, wherein the detected analog signal represents measurements of skull volumetric variation;
   c. a processor interfaced with the receiver, wherein the processor is configured to convert the detected analog signal to a digital signal and identify a trigger event from the digital signal, wherein an individual measurement in the analog signal is represented by a sequence of bits in the digital signal; and
   d. a transmitter interfaced with the processor, wherein the transmitter is configured to transmit the entire sequence of bits for a given measurement in the digital signal to a pre-configured receiver upon identifying the trigger event and to transmit only a subset of least significant bits from a sequence of bits for subsequent measurements in the digital signal until another trigger event is identified, wherein the transmitter and the pre-configured receiver communicate wirelessly.

10. The system according to claim 9, wherein the detection device comprises:
 a. the transducer of variation provided with a first end configured to receive a deflection related to the skull volumetric variation, wherein the transducer of variation converts a detected variation on electric signal; and
 b. a housing, wherein the transducer of variation is positioned inside the housing.

11. The system according to claim 9, wherein the pre-configured receiver is further capable to reconstruct an entire sequence of bits for a subsequent measurement.

12. The system according to claim 9, wherein the processor compares most significant bits of the digital signal to a predetermined threshold to identify when the detection device has been properly placed on the user's head; and the transmitter transmits the entire sequence of bits for the given measurement and subsequently transmits only a subset of the least significant bits for the subsequent measurements until removal of the detection device is detected.

13. A method for non-invasive management and monitoring of intracranial pressure, comprising:
 detecting, by a transducer of a detection device, volumetric variation of a skull of a person and generating an analog signal indicative of the volumetric variation, wherein the detection device, which further comprises an environmental sensor comprising a temperature sensor, and at least one of a gyroscope and an accelerometer, is configured to be placed on head of the person and the transducer is displaced by the volumetric variation;
 receiving, by a receiver, the analog signals from the detection device, wherein the analog signal represents measurements of volumetric variation;
 converting, by a signal processor, the analog signal to a digital signal, wherein each measurement in the analog signal is represented by a sequence of bits in the digital signal;
 detecting, by the signal processor, proper placement of the detection device on the head of the person using the digital signal;
 upon detecting proper placement, transmitting, by the transmitter, the entire sequence of bits for a given measurement in the digital signal;
 transmitting, by the transmitter, only a subset of least significant bits from a sequence of bits for subsequent measurements in the digital signal.

* * * * *